(12) United States Patent
Leveling et al.

(10) Patent No.: US 9,277,980 B2
(45) Date of Patent: Mar. 8, 2016

(54) MOUTHPIECE FOR CLEANING TEETH COMPRISED OF ALTERNATING LAYERS OF BASE AND BRISTLE COMPONENTS

(71) Applicant: KONINKLIJKE PHILIPS N.V., Eindhoven (NL)

(72) Inventors: Jurriaan Bernhard Rudolf Leveling, Emmen (NL); Folkert Vrijburg, Drachten (NL); Geert Hendrik Westrup, Sint Jansklooster (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/368,824

(22) PCT Filed: Dec. 18, 2012

(86) PCT No.: PCT/IB2012/057426
§ 371 (c)(1),
(2) Date: Jun. 26, 2014

(87) PCT Pub. No.: WO2013/098718
PCT Pub. Date: Jul. 4, 2013

(65) Prior Publication Data
US 2014/0373290 A1    Dec. 25, 2014

Related U.S. Application Data

(60) Provisional application No. 61/580,408, filed on Dec. 27, 2011.

(51) Int. Cl.
*A61C 17/22* (2006.01)

(52) U.S. Cl.
CPC ................................ *A61C 17/228* (2013.01)

(58) Field of Classification Search
CPC .... A61C 17/228; A61C 17/222; A61C 17/38; A46B 9/045
See application file for complete search history.

(56) References Cited

U.S. PATENT DOCUMENTS

| | | | |
|---|---|---|---|
| 8,359,692 B2 * | 1/2013 | Brewer | 15/22.1 |
| 8,990,992 B2 * | 3/2015 | Stapelbroek et al. | 15/22.1 |
| 2007/0181259 A1 | 8/2007 | Bar-Erez | |
| 2009/0276972 A1 * | 11/2009 | Dugan | 15/167.2 |

FOREIGN PATENT DOCUMENTS

| | | |
|---|---|---|
| CN | 1487803 A | 4/2004 |
| CN | 201356672 Y | 12/2009 |
| CN | 102056569 A | 5/2011 |
| DE | 8913203 U1 | 3/1991 |
| DE | 102005059775 A1 | 6/2007 |
| WO | 9934976 A1 | 7/1999 |
| WO | 0247512 A1 | 6/2002 |
| WO | 2008016342 A1 | 2/2008 |
| WO | 2009150559 A1 | 12/2009 |

* cited by examiner

*Primary Examiner* — Shay Karls

(57) ABSTRACT

The mouthpiece includes a plurality of individual thin layers of material forming a base or shell portion of the mouthpiece alternating with a plurality of individual bristle layers which are configured to the shape of bristles at the interior surfaces thereof. The base layers are comprised of a material which is sufficiently stiff to permit driving of the mouthpiece, while the bristle layers comprise material which is sufficiently flexible to produce an effective scrubbing action in operation without damage to the mouth tissues.

8 Claims, 3 Drawing Sheets

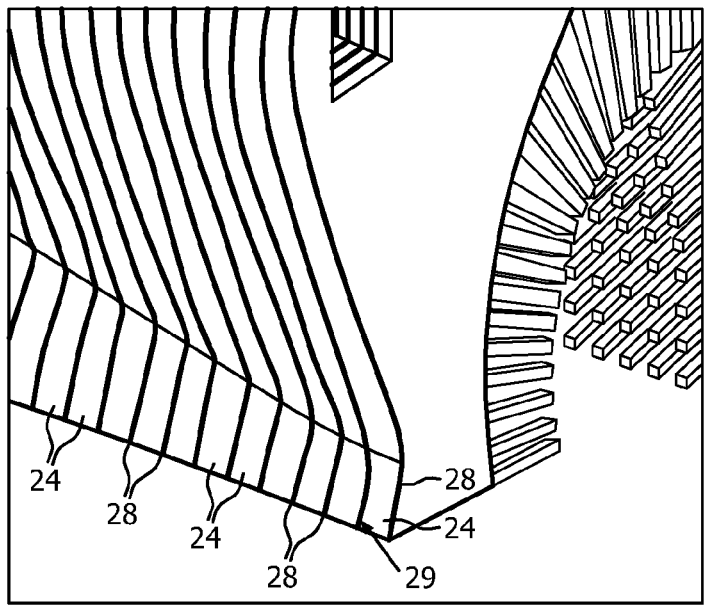
FIG. 3
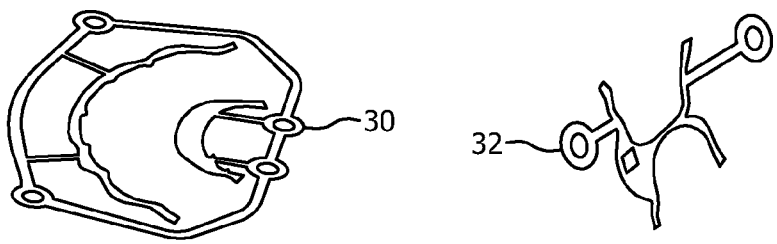
FIG. 4          FIG. 4A
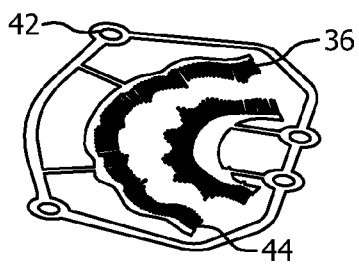   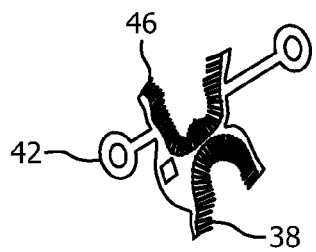
FIG. 5          FIG. 5A

MOUTHPIECE FOR CLEANING TEETH COMPRISED OF ALTERNATING LAYERS OF BASE AND BRISTLE COMPONENTS

CROSS-REFERENCE TO PRIOR APPLICATIONS

This application is the U.S. National Phase application under 35 U.S.C. §371 of International Application No. PCT/IB 2012/057426, filed on Dec. 18, 2012, which claims the benefit of U.S. Provisional Patent Application No. 61/580,408, filed on Dec. 27, 2011. These applications are hereby incorporated by reference herein.

This invention relates generally to mouthpiece appliances for cleaning teeth and more specifically concerns a composite structure for the mouthpiece.

One method for cleaning teeth involves the use of a toothbrush or a mouthpiece with bristles which move or are moved along the surfaces of the teeth to clean the teeth by scrubbing action. For a mouthpiece, which covers all of the teeth surfaces at once, the space within the mouth to accommodate the appliance is quite limited because the area around the teeth is restricted in volume by cheeks, lips, tongue and bone from the jaws and skull. Typically, the mouthpiece appliance includes a shell or base portion which is acted on by a driving assembly which includes a motor or similar member and a connecting structure to the base portion. The motor can be located either inside the mouth or external of the mouth. A set of bristles extends from or is positioned on the shell/base to produce the scrubbing action. The bristles should comprise a relatively flexible material to provide an effective brushing action while preventing irritation. The shell should comprise a relatively stiff material so that the bristles can be conveniently driven along the surfaces of the teeth. Two different types of material are thus needed to build an effective mouthpiece within a limited physical space.

FIG. 3 is a perspective view showing a close-up of a portion of FIG. 2.

FIGS. 4 and 4A show, respectively, base portion layers for the front teeth and the molar or back teeth.

FIGS. 5 and 5A show, respectively, bristle portion layers for the front teeth and the back or molar teeth.

Figure 1:
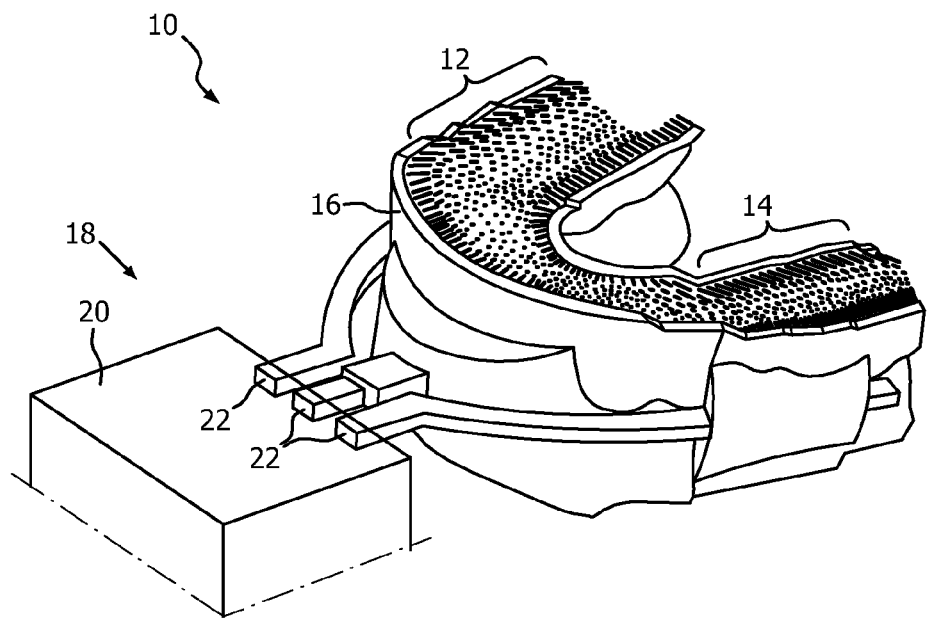
FIG. 1 is an isometric view of a multilayer mouthpiece described and shown herein.

FIG. 1 shows a mouthpiece, generally at 10, which includes two back or molar portions 12, 14 which are designed and configured to brush the molar teeth and perhaps one or so of the premolar teeth of the mouth, and a front portion 16 which is positioned intermediate of the two back portions 12, 14 and is designed and configured to brush the front teeth, generally from canine tooth on one side to canine tooth on the other side, and perhaps one or so of the premolars, depending on the particular mouthpiece arrangement. Also shown is a drive system 18 which in general comprises a motor 20 and three drive elements 22-22 which are secured to the individual back portions and the front portion and in operation move those portions in a way to produce a scrubbing or brushing action on the teeth. The drive system can have various configurations and arrangements in the present mouthpiece. The mouthpiece could also be driven by hand.

Figure 2:
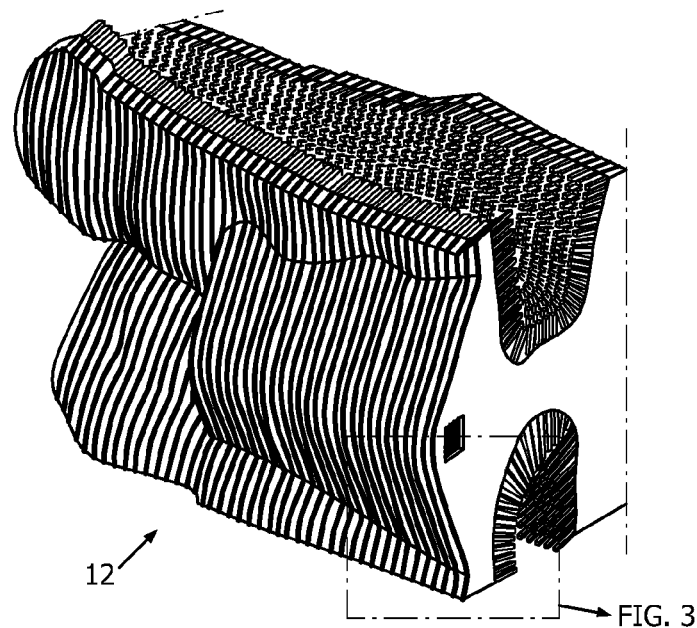
FIG. 2 is a perspective view of a portion of the mouthpiece showing the multilayer construction thereof.

In the present invention, the mouthpiece 10, comprising the two back portions 12, 14 and the front portion 16, comprises alternating thin layers of two different materials, with one of the layers so configured and comprising such a material as to form a sufficiently stiff base part of the front and back portions for driving the mouthpiece, while the other alternate layers comprise a more flexible material, configured to define bristle elements, to accomplish the cleaning of the teeth without discomfort. This arrangement of layers is shown generally in FIGS. 2 and 3, with FIG. 2 being a section of one of the back portions of the mouthpiece for both upper and lower jaw teeth, and FIG. 3 being a close-up of a portion of FIG. 2. FIGS. 2 and 3 show sections of the completed mouthpiece following stacked construction of the individual alternating layers sufficient in number to cover the teeth. Other mouthpiece arrangements are possible, e.g. a two arch arrangement, with one arch brushing the inside surfaces of the teeth and the other brushing the outside surfaces. In the embodiment shown, the base layers 24-24 comprise a PET (polyethylene terephthalate) material having a preferred thickness of approximately 0.5 mm. Other similar materials of similar stiffness can be used. The material must be sufficiently stiff to be able to support and accommodate a driving action with a connecting member, as well as, in the embodiment shown, being sufficiently thick and stiff that adhesive can be conveniently applied to both sides of the layer, instead of to the bristle layers. The adhesive can, however, certainly be applied to the bristle layers. The bristle layers 28-28 in the embodiment shown comprise a TPE (thermoplastic elastomer) material with a preferred thickness of 0.25 mm. This material comprises the bristles formed by a laser cutter and must be sufficiently flexible to provide a good brushing action, but not cause any discomfort. The PET base material layer 24 is typically 0.1-0.75 mm thick, while the TPE (bristle layer) 28 is 0.05-0.25 thick. Other materials similar to PET can be used, such as a polycarbonate plastic. The bristle stiffness can have a maximum characterized by deflection of no more than 50% with an applied bristle tip pressure of 85 Newtons per $cm^2$. The adhesive, which in construction of the mouthpiece is applied on opposing sides of the thicker PET material and shown at 29, is in the embodiment shown a polyethylene glue, approximately 0.05 mm thick, although other glues/adhesives can be used. Other ways of bonding the layers can be used, including welding, ultrasonic and RF.

FIGS. 4 and 4A show, respectively, the base layers 30, 32 (following laser cutting) for the front and rear portions of the mouthpiece, with alignment elements 34 for the stacking process. FIGS. 5 and 5A show, respectively, the bristle layers 36, 38 (following laser cutting) for the front and rear portions of the mouthpiece, with alignment elements 40. It should be understood that other ways of cutting the layers can be used.

Figure 6:
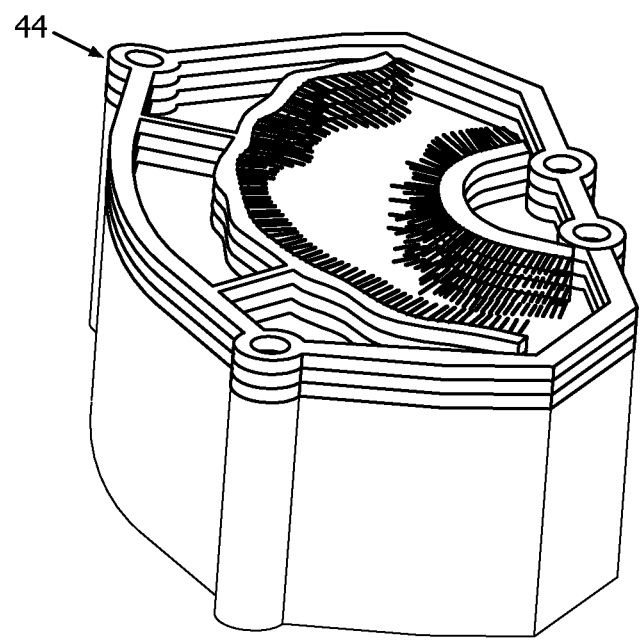
FIG. 6 is a perspective view of the front portion of the mouthpiece formed of the stacked base portion and bristle portion layers, with alignment elements.
Figure 7:
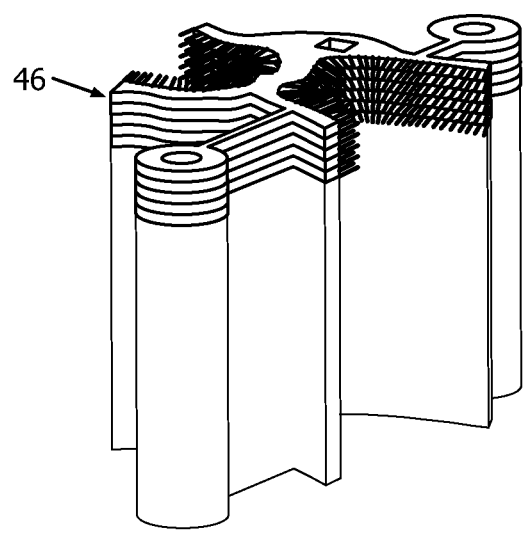
FIG. 7 is a perspective view of the back or molar portion of the mouthpiece formed of the stacked base portion and bristle portion layers with alignment elements.

The plurality of base layers 30, 32 for the front and rear portions are cut out using well-known laser process technology, referred to generally as laminated object manufacturing. The plurality of alternating bristle layers 36, 38 for the front and rear portions are also cut out using the laser technology. Other cutting techniques can be used. The layers 36, 38 are cut to form a plurality of individual bristles 44 and 46 in the front and back portions. In the embodiment shown, the length of the bristles is between 2.5-5 mm and are cut so as to extend away from the surface of the alternating base layers. The laser cutting of each layer is accomplished prior to the stacking and gluing (bonding) of the individual layers. The cut layers shown in FIGS. 4, 4A and 5, 5A are stacked alternately together to form the separate front and back portions of the workpiece. The individual layers are aligned by the alignment elements on each layer. The alignment elements are not needed if pick and place techniques are used. As indicated above, adhesive is applied to opposing sides of each base layer, and the base and bristle layers then are sequentially stacked together. The adhesive hardens to form stacked assemblies such as shown in assembly 44 in FIG. 6 for the front portion and FIG. 7 for the back portions of the workpiece. In each case, the laser cut bristles extend toward the teeth from the surface of the base layers. The alignment elements are then removed and the resulting surfaces of the front and back portions are smoothed such that they will not cause harm or discomfort to the mouth tissues or the gums of the user. Once the alignment sections are cut away, the front portion is secured to the two back portions to form the complete mouthpiece, as shown in FIG. 1.

One advantage of the present invention is that a mouthpiece can be readily customized to fit a particular individual's oral geometry, which is a significant challenge for conventional mouthpiece arrangements. In the custom process, a digital scan is made of a user's oral geometry. Again, digital scanning is well known, and there are several devices available which can provide a suitable digital oral scan. The scan data is then used to control the laser cutter to produce a mouthpiece custom arranged to the oral geometry of the user. The present invention thus provides not only an effective mouthpiece, but permits convenient customization of a mouthpiece configuration to fit the oral geometry of individual users.

Accordingly, a mouthpiece has been described and shown which comprises a plurality of alternating layers which are laser cut, or cut by other techniques, to form the desired mouthpiece configuration. One layer comprises a flexible bristle layer for scrubbing teeth, while the other alternating layer is of a stiffer material to form the base for driving of the mouthpiece. Mouthpieces which are customized for individual users are thus a convenient possibility.

Although a preferred embodiment of the invention has been disclosed for purpose of illustration, it should be understood that various changes, modifications, and substitutions may be incorporated in the embodiment without departing from the spirit of the invention which is defined by the claims that follow:

The invention claimed is:

1. A mouthpiece with multi-layer construction for cleaning teeth, comprising:
    a plurality of separate individual base layers configured to form base or shell portions of the mouthpiece, wherein each individual base layer comprises a stiff material so that it can be driven for brushing movement of the mouthpiece;
    a plurality of separate individual bristle layers configured for being positioned in an alternating arrangement between individual base layers, wherein each individual bristle layer comprises a single layer of individual bristle elements having free ends thereof for brushing teeth, wherein each layer of the plurality of alternating base and bristle layers are sequentially stacked, aligned and secured together in a stacked multi-layer assembly of individual alternating base and bristle layers to form a mouthpiece or portion thereof; and
    a drive assembly coupled to the stacked multi-layer assembly to accomplish a brushing action with the mouthpiece or portion thereof.

2. The mouthpiece of claim 1, wherein the front portion and the back or molar portions are further arranged to cover a user's teeth in both upper and lower jaws.

3. The mouthpiece of claim 1, wherein the base layers comprise a thermoplastic material, having a thickness in a range of 0.10-0.75 mm, and wherein the bristle layers comprise a flexible material capable of brushing teeth without harm to surrounding tissues, with a thickness in a range of 0.05-0.25 mm.

4. The mouthpiece of claim 3, further wherein the individual bristle elements have a length in a range of 2.5-5.0 mm.

5. The mouthpiece of claim 1, wherein the separate individual base and bristle layers comprise cut out layers formed by laser cutting.

6. The mouthpiece of claim 1, wherein a maximum bristle stiffness of the individual bristle elements is characterized by a deflection of no more than 50% with an applied bristle tip pressure of 85 Newtons per $cm^2$.

7. The mouthpiece of claim 1, wherein the drive assembly includes a motor and separate drive elements configured to couple the motor to (i) the front portion and (ii) the back or molar portions of the stacked multi-layer assembly.

8. The mouthpiece of claim 1, further comprising a customized mouthpiece configuration arranged to fit a particular user's oral geometry, wherein individual layers of the alternating base and bristle layers of the stacked multi-layer assembly are custom formed by laser cutting in response to digital oral scan data of the particular user's oral geometry.

* * * * *